United States Patent
Michel et al.

(10) Patent No.: US 6,465,672 B2
(45) Date of Patent: Oct. 15, 2002

(54) PROCESS FOR THE PRODUCTION OF ORGANOSILYLALKYL POLYSULFANES

(75) Inventors: Rudolf Michel, Freigericht; Jorg Munzenberg, Hanau; Werner Will, Gelnhausen; Gerd Rainhard Zezulka, Hanau, all of (DE)

(73) Assignee: Degussa AG, Frankfurt am Main (DE)

( * ) Notice: Subject to any disclaimer, the term of this patent is extended or adjusted under 35 U.S.C. 154(b) by 0 days.

(21) Appl. No.: 09/795,709

(22) Filed: Mar. 1, 2001

(65) Prior Publication Data

US 2001/0037034 A1 Nov. 1, 2001

(30) Foreign Application Priority Data

Mar. 1, 2000 (DE) .......................... 100 09 790

(51) Int. Cl.⁷ ................................................. C07F 7/08
(52) U.S. Cl. ...................................................... 556/427
(58) Field of Search ......................................... 556/427

(56) References Cited

U.S. PATENT DOCUMENTS

| | | | | |
|---|---|---|---|---|
| 3,842,111 A | * | 10/1974 | Meyer-Simon et al. | 556/427 |
| 3,978,103 A | * | 8/1976 | Meyer-Simon et al. | 556/427 |
| 4,048,206 A | | 9/1977 | Voronkov et al. | |
| 4,125,552 A | | 11/1978 | Speier | |
| 5,399,739 A | | 3/1995 | French et al. | |
| 5,489,701 A | | 2/1996 | Childress et al. | |
| 5,770,754 A | | 6/1998 | Scholl | |
| 5,859,275 A | | 1/1999 | Münzenberg et al. | |
| 5,892,085 A | | 4/1999 | Münzenberg et al. | |
| 6,066,752 A | * | 5/2000 | Takata et al. | 556/427 |
| 6,114,560 A | * | 9/2000 | Ichinohe et al. | 556/427 |
| 6,140,524 A | * | 10/2000 | Ichinohe et al. | 556/427 |
| 6,194,595 B1 | * | 2/2001 | Michel et al. | 556/427 |
| 6,274,755 B1 | * | 8/2001 | Munzenberg et al. | 556/427 |
| 2001/0037034 A1 | | 11/2001 | Michel et al. | |

FOREIGN PATENT DOCUMENTS

| | | |
|---|---|---|
| DE | 2 141 159 | 3/1973 |
| DE | 2 212 239 | 10/1973 |
| DE | 26 48 241 | 6/1977 |
| DE | 197 34 295 | 8/1997 |
| DE | 196 10 281 | 9/1997 |
| DE | 196 51 849 | 6/1998 |
| DE | 100 09 790 | 9/2001 |
| EP | 0 694 552 | 1/1996 |
| EP | 0 705 838 | 4/1996 |
| EP | 0 794 186 | 9/1997 |
| EP | 0 839 816 | 5/1998 |
| EP | 0 949 263 | 10/1999 |
| JP | 7-228588 | 7/1995 |

OTHER PUBLICATIONS

English language abstract of OR above.
English language abstract of PR above.
English language abstract of QR above.
English language abstract of RR above.
English language abstract of SR above.
English language abstract of XR above.
English language abstract of OR2 above.
English language abstract of PR2 above.
English language abstract of QR2 above.

* cited by examiner

Primary Examiner—Paul F. Shaver
(74) Attorney, Agent, or Firm—Pillsbury Winthrop LLP

(57) ABSTRACT

The invention relates to a process for the production of organosilylalkyl polysulfanes by reacting an organosilylalide alkyl halide and an anhydrous or virtually anhydrous ionic sulfide and elementary sulfur, wherein the elementary sulfur and organosilylalkyl halide are suspended in a polar organic solvent and the ionic sulfide is added to this suspension.

4 Claims, No Drawings

PROCESS FOR THE PRODUCTION OF ORGANOSILYLALKYL POLYSULFANES

This application claims priority from German Application No. 100 09 790.1, filed on Mar. 1, 2000, the subject matter of which is hereby incorporated herein by reference.

BACKGROUND OF THE INVENTION

1. Field of the Invention

The present invention relates to a process for the production of organosilylalkyl polysulfanes.

2. Background Information

It is known that organosilylalkyl polysulfanes such as bis(3-triethoxysilylpropyl)tetrasulfane (DE 2 141 159 and bis(3-triethoxysilylpropyl)disulfane can be used as silane coupling agent or reinforcing additive in rubber mixtures filled with oxides. The rubber mixtures are used, inter alia, for industrial rubber articles and for parts of vehicle tires, in particular for treads (DE 2 141 159, DE 2 212 239, U.S. Pat. No. 3,978,103, U.S. Pat. No. 4,048,206).

Various processes for producing organosilylalkyl polysulfanes are described in the literature. In this respect processes that use industrially easily accessible organosilylalkyl halides represent the most economical and simplest alternative. These organosilylalkyl halides are reacted with ionic polysulfides, whereby the halide functions of two molecules are replaced by polysulfane units by nucleophilic substitution and thereby bonded to one another.

In this process the preparation of the nucleophilic polysulfide presents the most difficulty. Of course, ionic polysulfides can be obtained relatively easily in aqueous phase according to a method known per se by reacting sulfur with alkali sulfide hydrates, alkali hydrogen sulfide hydrates or caustic soda and the resultant aqueous alkali polysulfide solutions can then be reacted with organosilylalkyl halides in a phase-transfer catalytic system to form the analogous polysulfanes (EP 694552, EP 794186, EP 839816). However, with the known process there is always the disadvantage that large proportions of the alkoxysilane starting material are converted into ineffective solid polysiloxanes due to hydrolysis and condensation. The organosilane polysulfides produced according to the known process are also characterised by an unsatisfactory storage stability.

These disadvantages can be avoided by working with anhydrous or virtually anhydrous starting substances in organic solution. U.S. Pat. No. 5,399,739 and EP 705838 disclose processes in which ionic polysulfides are produced by reacting alcoholates with hydrogen sulfide, which in turn are then reacted with sulfur and the corresponding organosilylalkyl halide. The disadvantage of these processes is that hydrogen sulfide gas, which is problematic from the safety and toxicological aspects, and alcoholates, which are not very stable under storage, are used in the production of the anhydrous sulfide.

A technically better solution for producing anhydrous or virtually anhydrous sulfides is to dry alkali sulfides, principally sodium sulfide hydrate, which are commercially available in large quantities. From JP 7228588 it is known that the drying process can be carried out azeotropically as well as in vacuo under heating, and the anhydrous or virtually anhydrous sulfides thus obtained can be reacted with sulfur to form alkali polysulfides. These polysulfides in turn react with organosilylalkyl halides to form the corresponding polysulfanes.

A similar process involving a variation of the azeotropic drying of the alkali sulfide is known from EP 795558.

The disadvantage of these processes however is that a polysulfide first of all has to be produced in a preceding process step from the alkali sulfide and sulfur, and can only then be converted by reaction with the organosilylalkyl halide into the desired polysulfide.

In DE 19651849 a process is described in which the production of the polysulfide already takes place during the drying. The process step involving the polysulfide production can thus be avoided and cost savings can be made, which significantly improves the economy of the process.

Further processes that likewise produce organosilylalkyl polysulfanes from anhydrous or virtually anhydrous ionic sulfides and that avoid a preliminary polysulfide production stage are described in DE 19734295 and EP 949263.

A common feature of all the cited processes is that an anhydrous polysulfide is mixed with a polar organic solvent and the organosilylalkyl halide is added to this solution/suspension. However, highly colored and often also unpleasantly smelling products are formed in such a procedure.

SUMMARY OF THE INVENTION

It is an object of the invention to provide a process in which organosilane polysulfides are produced that are only slightly colored and have only a slight unpleasant odor.

The present invention accordingly provides a process for the production of organosilylalkyl polysulfanes of the general formula $$R^1R^2R^3SiR^4)_2S_x \qquad (I)$$

in which
$R^1$, $R^2$, $R^3$, which are identical to or different from one another, denote branched and unbranched alkyl and/or alkoxy groups with a chain length of 1–8 C atoms, preferably 1–3 C atoms, aryl radicals, in particular phenyl, toluyl, benzyl, wherein at least one alkoxy group is present;
$R^4$ denotes a divalent alkylene radical with a chain length of 1 to 8 C atoms, preferably 1 to 5 C atoms, particularly preferably methylene, ethylene, i-propylene, n-propylene, i-butylene, n-butylene, n-pentylene, 2-methylbutylene, 3-methylbutylene, 1,3-dimethylpropylene and 2,3-dimethylpropylene, or —$(CH_2)_n$—$C_6H_4$—$(CH_2)_n$— where n=1–4;
x is a number >1, preferably between 2 and 6,
by reacting an organosilylalkyl halide of the general formula $$R^1R^2R^3SiR^4X \qquad (II)$$

in which
$R^1$, $R$ $R^3$ and $R^4$ have the meanings given above, and
X is chlorine, bromine or iodine,
and an anhydrous or virtually anhydrous ionic sulfide of the general formula $$M^+_2S^{2-} \qquad (III)$$

in which $M^+$ denotes an alkali metal cation, preferably a sodium or potassium cation, an ammonium ion, an alkaline earth metal cation or a zinc cation,
and elementary sulfur,
which is characterised in that the elementary sulfur and organosilylalkyl halide are placed in a polar organic solvent and the anhydrous or virtually anhydrous ionic sulfide is added to this suspension.

After the reaction the organosilylalkyl polysulfane can be isolated by filtering off the precipitated halide and separating the solvent by distillation.

On account of the susceptibility of the organosilylalkyl halide (II) to undergo hydrolysis, the ionic sulfides (III) must be anhydrous or virtually anhydrous. Virtually anhydrous ionic sulfides (III) are understood to be compounds according to formula (III) containing at most 10 wt. %, preferably 0–5 wt. %, and particularly preferably 0–2 wt. % of water. The virtually anhydrous ionic sulfides (III) can be obtained in various ways:

Reaction of alkali metal alcoholates with hydrogen sulfide (EP 0 705 838).

Reaction of ammonia gas with hydrogen sulfide (DE 26 48 241).

Drying alkali sulfide hydrates (DE 196 10 281, JP 7 228 588 and DE 196 51 849).

In this connection it is unimportant whether the drying of the alkali sulfide hydrates is carried out azeotropically or by heating in vacuo. Preferably, the required ionic sulfide may be prepared according to the process described in DE 196 51 849. The ionic sulfide (III) may, without influencing the reaction yield, be used as a ground powder as well as in the form of small platelets, such as are present in the case of the commercially available alkali sulfide hydrates.

The amount of ionic sulfide (III) necessary for the reaction may be added in one lot or in partial amounts to the suspension consisting of the solvent, organosilylalkyl halide (II) and elementary sulfur. The ionic sulfide (III) may be added continuously or discontinuously.

The sulfur may be added in solid form, for example as a commercially available sulfur powder, or granules, or in molten form.

In order to accelerate the course of the reaction the sulfur may be used in finely divided form, for example as finely ground sulfur powder or as fine droplets of atomised melt.

As organic solvent there may in principle be used all polar solvents in which the ionic sulfide (III) is at least partially soluble, and which do not react with the organosilylalkyl halide (II).

Linear or branched alcohols with 1–8 C atoms, such as for example methyl, ethyl, propyl, butyl or pentyl alcohol, cycloalkyl alcohols with 5–8 C atoms, phenol or benzyl alcohol, may preferably be used as organic solvent.

In order to avoid a transesterification, it may be more expedient to use the alcohol corresponding in each case to the groups $R^1$, $R^2$ and $R^3$. Optionally, it may also be advantageous to use a mixture of these alcohols, for example if different alkoxy groups $R^1$, $R^2$, $R^3$ are present in the compound II.

The molar ratios of the individual reactants to one another are governed by the mean sulfur chain length that is to be established in the organosilylalkyl polysulfane (I) to be produced therewith, and by the residual content of organosilylalkyl halides (II) that is to be present in the end product. Accordingly the molar ratio of the ionic sulfide of the formula (III) to the elementary sulfur that is used controls the mean polysulfane chain length in the end product. For the process according to the invention ionic sulfide:sulfur may be used in a molar ratio of at least 1:0.1, preferably 1:0.8 to 1:5.2.

The molar ratio of ionic sulfide to the organosilylalkyl halide determines the residual content of the starting material in the end product. For the process according to the invention a ratio of ionic sulfide to organosilylalkyl halide of 1:1 to 1:3 may be chosen, preferably a ratio of 1:1.5 to 1:2.2.

The reaction may be carried out with the exclusion of air and water (moisture) in order to suppress or largely avoid the formation of secondary products. The reaction may be carried out at elevated temperature. In this connection it is immaterial for the process according to the invention whether, in order to reach the reaction temperature, the reaction mixture is heated externally or is heated solely by the heat released due to the exothermic reaction. The reaction may be carried out between room temperature and 200° C., preferably between 40° C. and the boiling point of the solvent that is used. The reaction may be carried out under reduced pressure, normal pressure or slight superatmospheric pressure.

The organosilane polysulfides produced by the process according to the invention have the advantage that they are less colored and have a less unpleasant odor than the known organosilane polysulfides.

DETAILED DESCRIPTION OF THE INVENTION

COMPARISON EXAMPLE 1

Preparation of bis(triethoxysilylpropyl)disulfane 17.8 kg of virtually anhydrous sodium sulfide are mixed with 190 l of ethanol and added to an enameled 500 l capacity reactor. This is followed by the addition through a fine nozzle of 13.85 kg of sulfur in molten form. The mixture is heated to 50° C. and 190 l of 3-chloropropyltriethoxysilane are metered in within 10 minutes. On account of the exothermic reaction the temperature of the reactor contents rises to 74° C. A further 4.45 kg of virtually anhydrous sodium sulfide are added at this temperature. Three further portions of sodium sulfide are added at 5 minute intervals (i.e. each 5 minutes), the temperature of the reactor contents rising to 82° C. After completion of the sodium sulfide addition the reaction mixture is kept for 1.5 hours at 82–83° C. and the sodium chloride that has precipitated is separated after cooling the mixture. A yellow product is obtained after evaporating the reaction mixture in vacuo and renewed fine filtration. HPLC analysis confirms the presence of a product with a mean polysulfane chain length of 2.

EXAMPLE 1

Preparation of bis(triethoxysilylpropyl)disulfane 13.85 kg of sulfur in molten form is metered in through a fine nozzle into a mixture of 190 l of ethanol and 190 l of 3-chloropropyltriethoxysilane contained in the reactor of comparison example 1. 17.8 kg of virtually anhydrous sodium sulfide are then added, the temperature of the reactor contents rising to 60° C. due to the heat released in the exothermic reaction. Four further portions of in each case 4.45 kg of sodium sulfide are added starting at this temperature at 5 minute intervals. The temperature of the reactor contents rises further to 82° C. After completion of the sodium sulfide addition the reaction mixture is kept for a further 1.5 hours at 82–83° C. and then cooled. The reaction mixture is worked up as in comparison example 1. An almost water-white product is obtained. HPLC analysis confirms the presence of a polysulfane mixture with a mean chain length of 2.

EXAMPLE 2

Preparation of bis(triethoxysilylpropyl)disulfane 129 l of ethanol are placed in the reactor of comparison example 1, followed by the addition of 129 l of 3-chloropropyltriethoxysilane. 13.85 kg of sulfur in molten form is metered through a fine nozzle into the resultant mixture. 17.8 kg of virtually anhydrous sodium sulfide is next added. The temperature of the reactor contents rises to 60° C. on account of the exothermic reaction. 4 further portions of in each case 4.45 kg of sodium sulfide are added at this temperature at 5 minute intervals. The temperature of the reactor contents thereby rises to 82° C. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2.

EXAMPLE 3
Preparation of bis(triethoxysilylpropyl)disulfane 129 l of 3-chloropropyltriethoxysilane is placed in the reactor of comparison example 1. 129 l of ethanol is added thereto. 13.85 kg of sulfur in molten form is metered through a fine nozzle into the resultant mixture. 17.8 kg of virtually anhydrous sodium sulfide is then added. The temperature of the reactor contents rises to 60° C. on account of the exothermic reaction. 4 further portions of in each case 4.45 kg of sodium sulfide are added starting at this temperature at 5 minute intervals. The temperature of the reactor contents rises to 82° C. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2.

EXAMPLE 4
Preparation of bis(triethoxysilylpropyl)disulfane 129 l of ethanol is placed in the reactor of comparison example 1. 13.85 kg of sulfur in molten form is added through a fine nozzle. 129 l of 3-chloropropyltriethoxysilane is added to the mixture. 17.8 kg of virtually anhydrous sodium sulfide is then added. The temperature of the reactor contents rises to 60° C. on account of the exothermic reaction. 4 further portions of in each case 4.45 kg of sodium sulfide are added starting at this temperature at 5 minute intervals. The temperature of the reactor contents rises to 82° C. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2.

EXAMPLE 5
Preparation of bis(triethoxysilylpropyl)disulfane 129 l of 3-chloropropyltriethoxysilane is placed in the reactor of comparison example 1. 13.85 kg of sulfur in molten form is metered in through a fine nozzle. 129 l of ethanol is added to the mixture, followed by 17.8 kg of virtually anhydrous sodium sulfide. The temperature of the reactor contents rises to 60° C. on account of the exothermic reaction. 4 further portions of in each case 4.45 kg of sodium sulfide are added starting at this temperature at 5 minute intervals. The temperature of the reactor contents rises to 82° C. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2.

EXAMPLE 6
Preparation of bis(triethoxysilylpropyl)disulfane

A mixture of 129 l of ethanol and 129 l of 3-chloropropyltriethoxysilane is placed in the reactor of comparison example 1. 13.85 kg of sulfur in the form of granules is metered in, followed by the addition of 17.8 kg of virtually anhydrous sodium sulfide. The temperature of the reactor contents rises to 60° C. on account of the exothermic reaction. 4 further portions of in each case 4.45 kg of sodium sulfide are added starting at this temperature at 5 minute intervals. The temperature of the reactor contents rises to 82° C. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2.

EXAMPLE 7
Preparation of bis(triethoxysilylpropyl)disulfane 129 l of ethanol is placed in the reactor of comparison example 1, followed by the addition of 129 l of 3-chloropropyltriethoxysilane. 13.85 kg of sulfur in the form of granules is metered in to the resultant mixture. 17.8 kg of virtually anhydrous sodium sulfide is then added. The temperature of the reactor contents rises to 60° C. on account of the exothermic reaction. 4 further portions of in each case 4.45 kg of sodium sulfide are added starting at this temperature at 5 minute intervals. The temperature of the reactor contents rises to 82° C. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2.

EXAMPLE 8
Preparation of bis(triethoxysilylpropyl)disulfane 129 l of 3-chloropropyltriethoxysilane is placed in the reactor of comparison example 1, followed by the addition of 129 l of ethanol. 13.85 kg of sulfur in the form of granules is metered in to the resultant mixture. 17.8 kg of virtually anhydrous sodium sulfide is then added. The temperature of the reactor contents rises to 60° C. on account of the exothermic reaction. 4 further portions of in each case 4.45 kg of sodium sulfide are added starting at this temperature at 5 minute intervals. The temperature of the reactor contents rises to 82° C. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2.

EXAMPLE 9
Preparation of bis(triethoxysilylpropyl)disulfane 129 l of ethanol is placed in the reactor of comparison example 1. 13.85 kg of sulfur in the form of granules is then metered in. 129 l of 3-chloropropyltriethoxysilane is added to the mixture. 17.8 kg of virtually anhydrous sodium sulfide is then added. The temperature of the reactor contents rises to 60° C. on account of the exothermic reaction. 4 further portions of in each case 4.45 kg of sodium sulfide are added starting at this temperature at 5 minute intervals. The temperature of the reactor contents rises to 82° C. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2.

EXAMPLE 10
Preparation of bis(triethoxysilylpropyl)disulfane 129 l of 3-chloropropyltriethoxysilane is placed in the reactor of comparison example 1. 13.85 kg of sulfur in the form of granules is metered in. 129 l of ethanol is added to the mixture, followed by the addition of 17.8 kg of virtually anhydrous sodium sulfide. The temperature of the reactor contents rises to 60° C. on account of the exothermic reaction. 4 further portions of in each case 4.45 kg of sodium sulfide are added starting at this temperature at 5 minute intervals. The temperature of the reactor contents rises to 82° C. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2.

EXAMPLE 11

Preparation of bis(triethoxysilylpropyl)disulfane

A mixture of 129 l of ethanol and 129 l of 3-chloropropyltriethoxysilane is placed in the reactor of comparison example 1. 13.85 kg of sulfur in the form of a powder are metered in. 17.8 kg of virtually anhydrous sodium sulfide is then added. The temperature of the reactor contents rises to 60° C. on account of the exothermic reaction. 4 further portions of in each case 4.45 kg of sodium sulfide are added starting at this temperature at 5 minute intervals. The temperature of the reactor contents rises to 82° C. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2.

EXAMPLE 12

Preparation of bis(triethoxysilylpropyl)disulfane 129 l of ethanol is placed in the reactor of comparison example 1. 129 l of 3-chloropropyltriethoxysilane is added. 13.85 kg of sulfur in the form of a powder is metered in to the resultant mixture. 17.8 kg of virtually anhydrous sodium sulfide is then added. The temperature of the reactor contents rises to 60° C. on account of the exothermic reaction. 4 further portions of in each case 4.45 kg of sodium sulfide are added starting at this temperature at 5 minute intervals. The temperature of the reactor contents rises to 82° C. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2.

EXAMPLE 13

Preparation of bis(triethoxysilylpropyl)disulfane 129 l of 3-chloropropyltriethoxysilane is placed in the reactor of comparison example 1. 129 l of ethanol is added. 13.85 kg of sulfur in the form of a powder is metered in to the resultant mixture. 17.8 kg of virtually anhydrous sodium sulfide is then added. The temperature of the reactor contents rises to 60° C. on account of the exothermic reaction. 4 further portions of in each case 4.45 kg of sodium sulfide is added starting at this temperature at 5 minute intervals. The temperature of the reactor contents rises to 82° C. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2.

EXAMPLE 14

Preparation of bis(triethoxysilylpropyl)disulfane 129 l of ethanol is placed in the reactor of comparison example 1. 13.85 kg of sulfur in the form of a powder is metered in. 129 l of 3-chloropropyltriethoxysilane is added to the mixture. 17.8 kg of virtually anhydrous sodium sulfide is then added. The temperature of the reactor contents rises to 60° C. on account of the exothermic reaction. 4 further portions of in each case 4.45 kg of sodium sulfide are added starting at this temperature at 5 minute intervals. The temperature of the reactor contents rises to 82° C. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2.

EXAMPLE 15

Preparation of bis(triethoxysilylpropyl)disulfane 129 l of 3-chloropropyltriethoxysilane is placed in the reactor of comparison example 1. 13.85 kg of sulfur in the form of a powder is metered in. 129 l of ethanol is added to the mixture. 17.8 kg of virtually anhydrous sodium sulfide is then added. The temperature of the reactor contents rises to 60° C. on account of the exothermic reaction. 4 further portions of in each case 4.45 kg of sodium sulfide are added starting at this temperature at 5 minute intervals. The temperature of the reactor contents rises to 820° C. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2.

EXAMPLE 16

Preparation of bis(triethoxysilylpropyl)disulfane

A mixture of 129 l of ethanol and 129 l of 3-chloropropyltriethoxysilane is placed in the reactor of comparison example 1. 13.85 kg of sulfur in molten form is then metered in through a fine nozzle. 35.6 kg of virtually anhydrous sodium sulfide is then added. The temperature of the reactor contents rises to 82° C. on account of the exothermic reaction. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2, though the mixture has a high monosulfane content.

EXAMPLE 17

Preparation of bis(triethoxysilylpropyl)disulfane

A mixture of 129 l of ethanol and 129 l of 3-chloropropyltriethoxysilane is placed in the reactor of comparison example 1. 13.85 kg of sulfur in the form of granules is metered in. 35.6 kg of virtually anhydrous sodium sulfide is then added. The temperature of the reactor contents rises to 82° C. on account of the exothermic reaction. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2, though the mixture has a high monosulfane content.

EXAMPLE 18
Preparation of bis(triethoxysilylpropyl)disulfane

A mixture of 129 l of ethanol and 129 l of 3-chloropropyltriethoxysilane is placed in the reactor of comparison example 1. 13.85 kg of sulfur in the form of a powder are metered in. 35.6 kg of virtually anhydrous sodium sulfide is then added. The temperature of the reactor contents rises to 82° C. on account of the exothermic reaction. The reaction mixture is kept for a further 1.5 hours at 82–83° C. and then cooled. The reaction mixture is worked up as in comparison example 1. An almost water-white product is obtained. HPLC analysis confirms in this case too the presence of a polysulfane mixture with a mean chain length of 2, though the mixture has a high monosulfane content.

COMPARISON EXAMPLE 2
Preparation of bis(triethoxysilylpropyl)tetrasulfane 23 kg of virtually dry sodium sulfide in 125 l of ethanol is placed in the reactor of comparison example 1. 28.4 kg of sulfur in molten form is added through a fine nozzle. The mixture is heated to 55° C. and 129 l of 3-chloropropyltriethoxysilane are metered in at this temperature within 50 minutes. The temperature of the reactor contents rises to 77° C. on account of the heat released in the exothermic reaction. The reaction mixture is kept for a further 1.5 hours at 82–83° C. and then cooled. Precipitated sodium chloride is separated. An orange product is obtained after evaporating the reaction mixture in vacuo and renewed fine filtration. HPLC analysis confirms the presence of a product with a mean polysulfane chain length of 4.

EXAMPLE 19
Preparation of bis(triethoxysilylpropyl)tetrasulfane 28.4 kg of sulfur in molten form is metered through a fine nozzle into a mixture of 129 l of ethanol and 129 l of 3-chloropropyltriethoxysilane contained in the reactor of comparison example 1. 23.0 kg of virtually anhydrous sodium sulfide is then added, the temperature of the reactor contents rising to 83° C. on account of the heat released in the exothermic reaction. The reaction mixture is kept for a further 1.5 hours at 82–83° C. and then cooled. The reaction mixture is worked up as in comparison example 1. A yellow product is obtained. HPLC analysis confirms the presence of a polysulfane mixture with a mean chain length of 4.

EXAMPLE 20
Preparation of bis(triethoxysilylpropyl)tetrasulfane 129 l of ethanol is placed in the reactor of comparison example 1. 129 l of 3-chloropropyltriethoxysilane is added thereto. 28.4 kg of sulfur in molten form is metered through a fine nozzle into the resultant mixture. 23.0 kg of virtually anhydrous sodium sulfide is then added. The temperature of the reactor contents rises to 83° C. due to the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 21
Preparation of bis(triethoxysilylpropyl)tetrasulfane 129 l of 3-chloropropyltriethoxysilane is placed in the reactor of comparison example 1. 129 l of ethanol is added thereto. 28.4 kg of sulfur in molten form is metered through a fine nozzle into the resultant mixture. 23.0 kg of virtually anhydrous sodium sulfide is then added. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 22
Preparation of bis(triethoxysilylpropyl)tetrasulfane 129 l of ethanol is placed in the reactor of comparison example 1. 28.4 kg of sulfur in molten form is metered in through a fine nozzle. 129 l of 3-chloropropyltriethoxysilane is added to the resultant mixture. 23.0 kg of virtually anhydrous sodium sulfide is then added. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 23
Preparation of bis(triethoxysilylpropyl)tetrasulfane 129 l of 3-chloropropyltriethoxysilane is placed in the reactor of comparison example 1. 28.4 kg of sulfur in molten form is metered in through a fine nozzle. 129 l of ethanol is added to the resultant mixture. 23.0 kg of virtually anhydrous sodium sulfide is then added. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 24
Preparation of bis(triethoxysilylpropyl)tetrasulfane 129 l of ethanol is placed in the reactor of comparison example 1. 129 l of 3-chloropropyltriethoxysilane is added thereto. 28.4 kg of sulfur in the form of granules is metered in to the resultant mixture. 23.0 kg of virtually anhydrous sodium sulfide is then added. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 25
Preparation of bis(triethoxysilylpropyl)tetrasulfane 129 l of 3-chloropropyltriethoxysilane is placed in the reactor of comparison example 1. 129 l of ethanol is added thereto. 28.4 kg of sulfur in the form of granules is metered in to the resultant mixture. 23.0 kg of virtually anhydrous sodium sulfide is then added. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 26
Preparation of bis(triethoxysilylpropyl)tetrasulfane 129 l of ethanol is placed in the reactor of comparison example 1. 28.4 kg of sulfur in the form of granules is metered in. 129 l of 3-chloropropyltriethoxysilane is added to the resultant mixture. 23.0 kg of virtually anhydrous sodium sulfide is then added. The temperature of the reactor contents rises to 83° C. on account of the exothermic reaction. The reaction mixture is kept for a 25 further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 27
Preparation of bis(triethoxysilylpropyl)tetrasulfane 129 l of 3-chloropropyltriethoxysilane is placed in the reactor of comparison example 1. 28.4 kg of sulfur in the form of granules is metered in. 129 l of ethanol is added to the resultant mixture. 23.0 kg of virtually anhydrous sodium sulfide is then added. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 28
Preparation of bis(triethoxysilylpropyl)tetrasulfane 129 l of ethanol is placed in the reactor of comparison example 1. 129 l of 3-chloropropyltriethoxysilane is added thereto. 28.4 kg of sulfur in the form of a powder is metered in to the resultant mixture. 23.0 kg of virtually anhydrous sodium sulfide is then added. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 29
Preparation of bis(triethoxysilylpropyl)tetrasulfane 129 l of 3-chloropropyltriethoxysilane is placed in the reactor of comparison example 1. 129 l of ethanol is added thereto. 28.4 kg of sulfur in the form of a powder is metered in to the resultant mixture. 23.0 kg of virtually anhydrous sodium sulfide is then added. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 30
Preparation of bis(triethoxysilylpropyl)tetrasulfane 129 l of ethanol is placed in the reactor of comparison example 1. 28.4 kg of sulfur in the form of a powder is metered in. 129 l of 3-chloropropyltriethoxysilane is added to the resultant mixture. 23.0 kg of virtually anhydrous sodium sulfide are then added. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 31
Preparation of bis(triethoxysilylpropyl)tetrasulfane 129 l of 3-chloropropyltriethoxysilane is placed in the reactor of comparison example 1. 28.4 kg of sulfur in the form of a powder are added thereto. 129 l of ethanol is added to the resultant mixture. 23.0 kg of virtually anhydrous sodium sulfide is then added. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 32
Preparation of bis(triethoxysilylpropyl)tetrasulfane 28.4 kg of sulfur in molten form is metered through a fine nozzle into a mixture of 129 l of ethanol and 129 l of 3-chloropropyltriethoxysilane in the reactor of comparison example 1. A total of 23.0 kg of virtually anhydrous sodium sulfide is then added in 10 equal portions at 7 minute intervals (i.e. each 7 minutes). The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 33
Preparation of bis(triethoxysilylpropyl)tetrasulfane 129 l of ethanol is placed in the reactor of comparison example 1. 129 l of 3-chloropropyltriethoxysilane is added thereto. 28.4 kg of sulfur in molten form is metered through a fine nozzle in to the resultant mixture. A total of 23.0 kg of virtually anhydrous sodium sulfide is then added in 10 equal portions at 7 minute intervals. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 34
Preparation of bis(triethoxysilylpropyl)tetrasulfane 129 l of 3-chloropropyltriethoxysilane is placed in the reactor of comparison example 1. 129 l of ethanol is added thereto. 28.4 kg of sulfur in molten form is metered through a fine nozzle into the resultant mixture. A total of 23.0 kg of virtually anhydrous sodium sulfide is then added in 10 equal portions at 7 minute intervals. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 35
Preparation of bis(triethoxysilylpropyl)tetrasulfane 129 l of ethanol is placed in the reactor of comparison example 1. 28.4 kg of sulfur in molten form is added thereto through a fine nozzle. 129 l of 3-chloropropyltriethoxysilane is added to the resultant mixture. A total of 23.0 kg of virtually anhydrous sodium sulfide is then added in 10 equal portions at 7 minute intervals. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 36
Preparation of bis(triethoxysilylpropyl)tetrasulfane 129 l of 3-chloropropyltriethoxysilane is placed in the reactor of comparison example 1. 28.4 kg of sulfur in molten form is metered in through a fine nozzle. 129 l of ethanol is added to the resultant mixture. A total of 23.0 kg of virtually anhydrous sodium sulfide is then added in 10 equal portions at 7 minute intervals. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 37
Preparation of bis(triethoxysilylpropyl)tetrasulfane 28.4 kg of sulfur in the form of granules is metered in to a mixture of 129 l of ethanol and 129 l of 3-chloropropyltriethoxysilane in the reactor of comparison example 1. A total of 23.0 kg of virtually anhydrous sodium sulfide is then added in 10 equal portions at 7 minute intervals. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 38
Preparation of bis(triethoxysilylpropyl)tetrasulfane 129 l of ethanol is placed in the reactor of comparison example 1. 129 l of 3-chloropropyltriethoxysilane is added thereto. 28.4 kg of sulfur in the form of granules is metered in to the resultant mixture. A total of 23.0 kg of virtually anhydrous sodium sulfide are then added in 10 equal portions at 7 minute intervals. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 39
Preparation of bis(triethoxysilylpropyl)tetrasulfane 129 l of 3-chloropropyltriethoxysilane is placed in the reactor of comparison example 1. 129 l of ethanol is added thereto. 28.4 kg of sulfur in the form of granules is metered in to the resultant mixture. A total of 23.0 kg of virtually anhydrous sodium sulfide is then added in 10 equal portions at 7 minute intervals. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 40
Preparation of bis(triethoxysilylpropyl)tetrasulfane 129 l of ethanol is placed in the reactor of comparison example 1. 28.4 kg of sulfur in the form of granules is metered in. 129 l of 3-chloropropyltriethoxysilane is added to the resultant mixture. A total of 23.0 kg of virtually anhydrous sodium sulfide is then added in 10 equal portions at 7 minute intervals. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 41
Preparation of bis(triethoxysilylpropyl)tetrasulfane 129 l of 3-chloropropyltriethoxysilane is placed in the reactor of comparison example 1. 28.4 kg of sulfur in the form of granules is metered in. 129 l of ethanol is added to the resultant mixture. A total of 23.0 kg of virtually anhydrous sodium sulfide is then added in 10 equal portions at 7 minute intervals. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 42
Preparation of bis(triethoxysilylpropyl)tetrasulfane 28.4 kg of sulfur in the form of a powder is metered in to a mixture of 129 l of ethanol and 129 l of 3-chloropropyltriethoxysilane in the reactor of comparison example 1. A total of 23.0 kg of virtually anhydrous sodium sulfide is then added in 10 equal portions at 7 minute intervals. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 43
Preparation of bis(triethoxysilylpropyl)tetrasulfane 129 l of ethanol is placed in the reactor of comparison example 1. 129 l of 3-chloropropyltriethoxysilane is added thereto. 28.4 kg of sulfur in the form of a powder is metered in to the resultant mixture. A total of 23.0 kg of virtually anhydrous sodium sulfide is then added in 10 equal portions at 7 minute intervals. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 44

Preparation of bis(triethoxysilylpropyl)tetrasulfane 129 l of 3-chloropropyltriethoxysilane is placed in the reactor of comparison example 1. 129 l of ethanol is added thereto. 28.4 kg of sulfur in the form of a powder is metered in to the resultant mixture. A total of 23.0 kg of virtually anhydrous sodium sulfide is then added in 10 equal portions at 7 minute intervals. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 45

Preparation of bis(triethoxysilylpropyl)tetrasulfane 129 l of ethanol is placed in the reactor of comparison example 1. 28.4 kg of sulfur in the form of a powder is metered in. 129 l of 3-chloropropyltriethoxysilane is added to the resultant mixture. A total of 23.0 kg of virtually anhydrous sodium sulfide is then added in 10 equal portions at 7 minute intervals. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

EXAMPLE 46

Preparation of bis(triethoxysilylpropyl)tetrasulfane 129 l of 3-chloropropyltriethoxysilane is placed in the reactor of comparison example 1. 28.4 kg of sulfur in the form of a powder is metered in. 129 l of ethanol is added to the resultant mixture. A total of 23.0 kg of virtually anhydrous sodium sulfide is then added in 10 equal portions at 7 minute intervals. The temperature of the reactor contents rises to 83° C. on account of the exothermic reaction. The reaction mixture is kept for a further 1.5 hours at 82–83° C. and then cooled. The reaction mixture is worked up as in comparison example 1. A yellow product is obtained. HPLC analysis confirms in this case too the presence of a polysulfane mixture with a mean chain length of 4.

What is claimed is:

1. A process for the production of organosilylalkyl polysulfanes of the general formula $(R^1R^2R^3SiR^4)_2S_x$ (I), in which:

$R^1$, $R^2$, $R^3$, are identical to or different from one another, and are branched or unbranched alkyl and/or alkoxy groups with a chain length of 1–8 carbon atoms, or aryl radicals, and wherein at least one alkoxy group is present;

$R^4$ is a divalent alkylene radical with a chain length of 1–8 C atoms, or $-(CH_2)_n-C_6H_4-(CH_2)_2-$, where n=1–4; and x is a number greater than 1;

said process comprising reacting an organosilylalkyl halide of the general formula $R^1R^2R^3SiR^4X$ (II), in which $R^1$, $R^2$, $R^3$ and $R^4$ have the meanings given above, and X is chlorine, bromine or iodine, with:

a) an anhydrous or virtually anhydrous ionic sulfide of the general formula $M^+_2S^{2-}$ (III), in which $M^+$ denotes an alkali metal cation, an ammonium ion, an alkaline earth metal cation or a zinc cation; and b) elementary sulfur;

wherein the elementary sulfur and organosilylalkyl halide are placed in a polar organic solvent and the anhydrous or virtually anhydrous ionic sulfide is added to this suspension.

2. The process of claim of claim 1, wherein $R^4$ is $-CH_2-CH_2-CH_2-$.

3. The process of either claim 1 or 2, wherein said ionic sulfide contains no more than 10 wt. % of water.

4. The process of either claim 1 or 2, wherein linear or branched alcohols with 1–8 carbon atoms are used as said organic solvent.

* * * * *